United States Patent [19]
Flaherty et al.

[11] Patent Number: 5,695,490
[45] Date of Patent: Dec. 9, 1997

[54] IMPLANTABLE TREATMENT MATERIAL DEVICE

[75] Inventors: J. Christopher Flaherty, Topsfield; David McDonald, Watertown; William J. Gorman, Essex, all of Mass.

[73] Assignee: Strato/Infusaid, Inc., Norwood, Mass.

[21] Appl. No.: 472,544

[22] Filed: Jun. 7, 1995

[51] Int. Cl.$^6$ ..................................................... A61M 5/14
[52] U.S. Cl. ................ 604/891.1; 604/93; 128/DIG. 12
[58] Field of Search ................................ 604/86, 88, 123, 604/124, 126, 93, 175, 891.1; 128/DIG. 12

[56] References Cited

U.S. PATENT DOCUMENTS

| | | |
|---|---|---|
| 4,496,343 | 1/1985 | Prosl et al. . |
| 4,573,994 | 3/1986 | Fischell et al. . |
| 5,137,529 | 8/1992 | Watson et al. . |
| 5,185,003 | 2/1993 | Brethauer . |
| 5,476,460 | 12/1995 | Montalvo .................. 604/891.1 |

FOREIGN PATENT DOCUMENTS

| | | |
|---|---|---|
| 0 110 117 A2 | 6/1984 | European Pat. Off. . |
| 4129782 | 10/1992 | Germany . |
| 2 121 690 | 1/1984 | United Kingdom . |
| 2131496 | 6/1984 | United Kingdom . |

OTHER PUBLICATIONS

PORT–A–CATH® Epidural Implantable Access System Instruction for Use, ©1991 Pharmacia Deltec Inc., St. Paul, MN 55112.
PORT–A–CATH® Epidural Implantable Access System, Patient Information, ©1991 Pharmacia Deltec Inc., St. Paul, MN 55112.
PORT–A–CATH® Implantable Epidural Access System, Journal Ad, ©1991 Pharmacia Deltec Inc., St. Paul, MN 55112.
CELSA–LG, Detail Aid, Avenue des Temps Modernes, FRANCE.

*Primary Examiner*—Corrine M. McDermott
*Attorney, Agent, or Firm*—Lappin & Kusmer LLP

[57] ABSTRACT

An implantable access device suitable for delivering a liquid medication to a site remote from the site of port implantation is disclosed, which contains a filter assembly for removing particulate material from fluid injected into the port. The filter assembly of the invention contains a first reservoir chamber having cutouts, recesses, and/or sharp corners in which particulate material may be trapped, and additionally having a first wall forming a filter barrier capable of 360° of fluid flow therethrough. The implantable access device may also include an infusion pump apparatus coupled to the access device. A filter assembly for insertion into an implantable treatment material device is also described.

32 Claims, 6 Drawing Sheets

IMPLANTABLE TREATMENT MATERIAL DEVICE

The present invention relates to implantable reservoirs for providing a treatment material, such as a drug in fluid form, directly to an internal site of a patient. More specifically, the invention relates to an implantable reservoir containing a filtering means to remove particulate matter and bacteria from fluid injected into the reservoir.

BACKGROUND OF THE INVENTION

Implantable devices have been developed for infusion or delivery of medications into a specific body site, for example, to avoid repeated intravenous, intrathecal, or epidural injections and thereby to minimize discomfort to a patient. Such devices generally include a housing containing an internal reservoir or chamber with an outlet cannula for connection to a catheter, and a penetrable reseatable septum, all of which are biocompatible. The devices may be implanted subcutaneously, with the septum oriented just under the skin to provide easy access to repeated needle penetration. A catheter generally connects the outlet cannula of the device to a site remote from the site of implantation. Medication may be injected through the septum into the reservoir of the device, thus allowing delivery of the medication directly to the remote treatment site.

Some medical conditions require installation of a pump drug delivery device in the body of the patient which is capable of delivering medication into a remote site through a catheter over a prolonged period of time. For example, chronic pain patients may receive such a pump for delivery of analgesics directly into the central nervous system via the spinal fluid. Such an access device may also be installed to replenish medication supply to a pump drug delivery device.

Conventional intraspinal access devices are generally similar to other implantable treatment reservoirs for injecting drugs or withdrawing blood samples, such as central venous access devices. All of those devices include a biocompatible housing containing an internal chamber or reservoir in fluid communication with the treatment site, i.e., the vascular system, intrathecal space, or epidural space, through a catheter, and a septum capable of resealing after being punctured by a needle. Intraspinal access devices of the prior art may develop blockages from particulate matter such as metal filings from needles and other metal present or from parts of the septum which may slough off as a result of needle puncture. Presently available intraspinal access devices and systems include filters which may be between the syringe and the needle or in the device itself.

Several kinds of filters are currently available. One kind, for access devices having a generally cylindrical internal reservoir with the exit port extending from a point on the cylindrical side surface of the reservoir, comprises a cylindrical screen positioned in the reservoir and having a diameter substantially equal to the inner diameter of the reservoir. A second kind, for access devices having an exit port extending from a point on the bottom surface of the reservoir, includes a mesh screen positioned on the bottom surface of the reservoir. These kinds of intraspinal access device filters are not capable of screening out much particulate matter, because the mesh of such filters is necessarily large in order to accommodate a satisfactory flow rate. One problem with a finer mesh is that needles injected into the septum of the device would cause more significant damage to the screen. A second problem is that the screens are placed directly adjacent to the outlet port, allowing only a small area of the screen to permit flow-through of fluid from the device, i.e., and that small area of flow-through is easily clogged. Also the fluid impedance is relatively high for small area filters.

U.S. Pat. No. 5,137,529 discloses an injection device containing a filter barrier extending across the internal injection chamber and separating the injection chamber into an upper portion adjacent to the septum and a lower portion in open fluid communication with the outlet conduit of the device.

U.S. Pat. No. 5,185,003 discloses a device for injecting medicaments containing a circular cylindrical filter member having a conical inner wall and being exactly adapted to fit the diameter of the inner cavity of the port. Another embodiment disclosed in U.S. Pat. No. 5,185,003 includes a filter member in the form of a plane-parallel disc between the inner cavity of the port and the outlet opening to the catheter.

A need exists, therefore, for an implantable treatment access device capable of filtering particulate matter out of medication being delivered to a specific body site.

One object of the invention is to provide an implantable treatment access device which is capable of removing debris from fluid injected therein.

Another object of the invention is to provide a filter assembly suitable for insertion into an implantable treatment access device, the filter assembly being capable of removing debris from fluid injected therein.

Another object of the invention is to provide an intraspinal access device for intrathecal or epidural delivery of medications which are substantially free of particulate material.

SUMMARY OF THE INVENTION

The present invention provides a multi-chambered implantable device including an access device having improved filtering capabilities. The implantable access device of the invention includes a biocompatible housing which defines an internal open-faced reservoir, preferably substantially cylindrical; a biocompatible, self-resealing, penetrable septum affixed to the housing and spanning the open face of the reservoir; an outlet cannula extending from the housing and adapted to receive a catheter, the outlet cannula defining an internal channel extending from a point on the internal wall of the reservoir; and a filter assembly disposed in the reservoir. The filter assembly of the invention includes a toroidal fluid permeable first wall, preferably a substantially cylindrical shell interior to and spaced apart from the lateral surface of the reservoir. In one form, the diameter of the first wall is sufficiently smaller than the inner diameter of the reservoir to allow a full 360° of fluid flow through the first wall, effectively utilizing substantially all of the surface area of the first wall as a filter barrier, in contrast to the limited surface area of known injection device filters. Placement of the first wall establishes two chambers: a first annular chamber between the first wall and the lateral surface of the housing reservoir; and a first reservoir chamber interior to the first wall and underlying the septum. The first annular chamber and the first reservoir chamber are in fluid communication only through the filter assembly's first wall, and the outlet cannula channel is in direct fluid communication only with the first annular chamber. In some embodiments, the filter assembly of the invention comprises a one-stage filter; for example, a one-stage filter is formed by filter assemblies having only a first wall. In other embodiments a substantially cylindrical, fluid permeable second wall may be provided to form a two-stage filter assembly, the second wall being placed interior to and spaced apart from the first filter assembly wall. The diameter of the second wall is sufficiently smaller than the diameter of the first wall to allow a full 360° of fluid flow through the second wall, allowing substantially all of the surface area of the second wall to be useful as a filter barrier. In these embodiments, the second wall forms an additional, second annular chamber within the first reservoir chamber.

In accordance with the present invention, fluid injected through the septum into the filter assembly flows from the first reservoir chamber through the substantially cylindrical first wall, into the first annular chamber formed by the first wall of the filter assembly and the inner wall of the reservoir. Fluid then flows from the first annular chamber to the outlet cannula to the treatment site. In those embodiments having a second wall and second annular chamber, injected fluid flows from the first reservoir chamber through the second wall into the second annular chamber, through the first wall to the first annular chamber and thence to the outlet cannula channel. In accordance with the present invention, fluid has no direct access from the first reservoir chamber to the outlet cannula channel.

The implantable device of the invention functions to filter debris out of fluid injected therein. The invention uses fluid dynamics created by the shape of the walls of the first reservoir chamber to trap particles in specifically designed cutouts, recesses, and/or sharp corners. When the port is accessed by a needle and fluid is injected into the filter assembly, a fluid flow is established in the first reservoir chamber which promotes accumulation of particulate matter from the fluid into the cutouts, recesses, and/or sharp corners. The cutouts, recesses, and/or sharp corners create static areas of fluid flow (dead space) or eddy flow paths in which particulate material accumulates. In accordance with the invention, the configuration of the cutouts, recesses, and/or sharp corners of the first reservoir chamber may be varied to optimize entrapment of particulate material. Thus using the implantable treatment material device of the invention, mainly particulate-free material is delivered to the treatment site. The implantable device of the invention is especially suitable as an intraspinal access device for epidural or intrathecal administration of drugs.

In one embodiment, the invention provides an implantable access device comprising:

A. a biocompatible housing defining an internal open-faced substantially cylindrical reservoir defined by a lateral surface extending about a central axis and a bottom surface;

B. a biocompatible, self-resealing, penetrable septum affixed to said housing and spanning the open face of said reservoir;

C. an outlet extending through said housing along an outlet channel axis from a point on said lateral surface of said reservoir; and D. a filter assembly disposed in said reservoir, said filter assembly including a substantially cylindrical fluid permeable first wall interior to and spaced apart from said lateral surface of said reservoir, said first wall establishing a first annular chamber between said first wall and said lateral surface and a first reservoir chamber interior to said first wall and underlying said septum, said first annular chamber and said first reservoir chamber being in fluid communication only through said first wall, and said outlet being in direct fluid communication with said first annular chamber.

In another embodiment, the invention provides a filter assembly comprising a substantially cylindrical fluid permeable first wall having a diameter sufficiently smaller than the inner diameter of an internal reservoir of an implantable access device to allow 360° of fluid flow therethrough, the first wall defining a first reservoir chamber having sharp corners therein.

BRIEF DESCRIPTION OF THE DRAWINGS

The foregoing and other objects of this invention, the various features thereof, as well as the invention itself, may be more fully understood from the following description, when read together with the accompanying drawings in which.

In the various figures, corresponding elements are denoted by the same reference designations.

DESCRIPTION OF THE PREFERRED EMBODIMENTS

Figure 1:
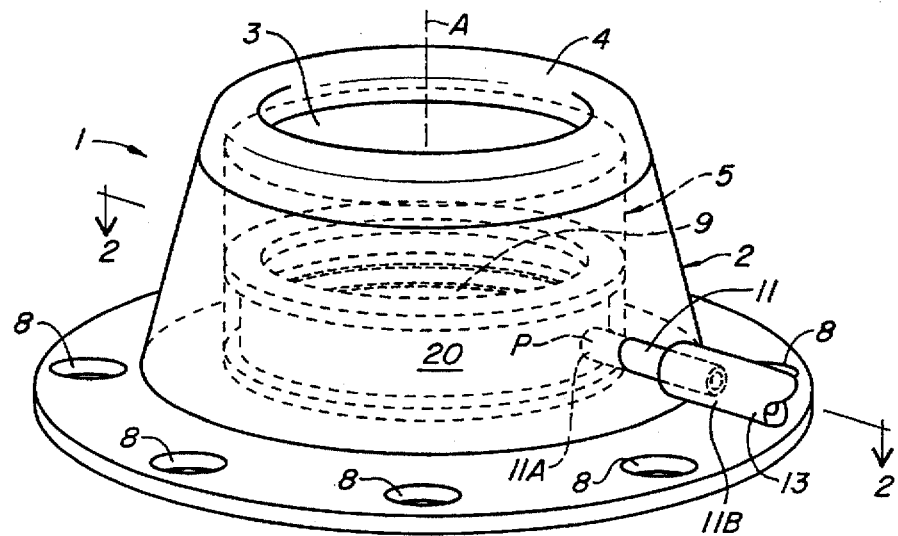
FIG. 1 shows an implantable two-stage after access device of the invention with an internal reservoir and filter assembly.
Figure 2:
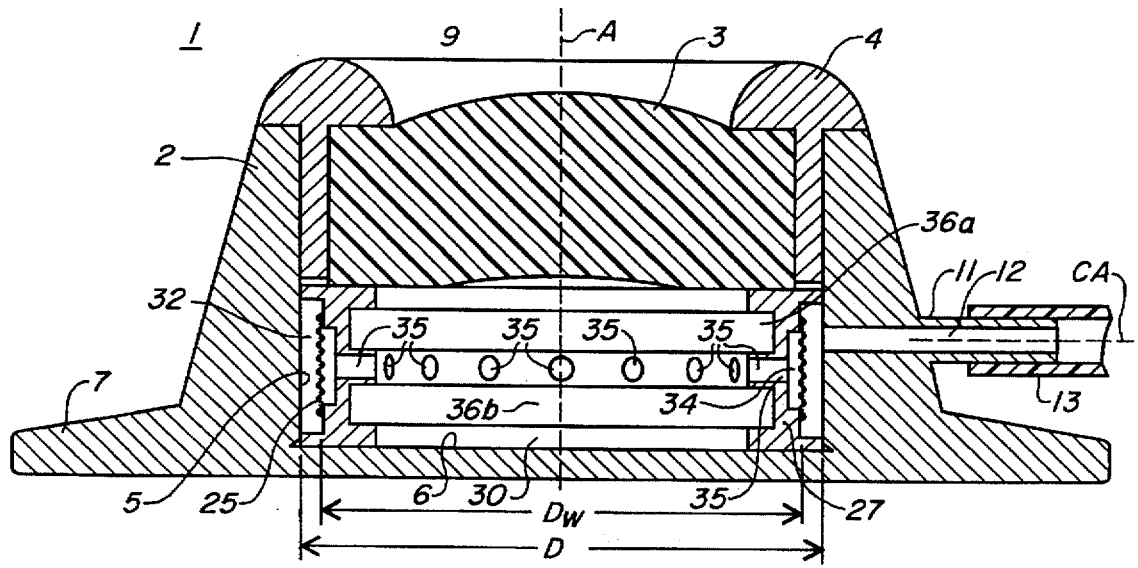
FIG. 2 shows a sectional view of the device of FIG. 1, taken along line 2—2.

The invention as depicted in FIGS. 1 and 2, includes a device 1 having a biocompatible housing 2 having a radially extending base flange plate 7 in which there are a multiplicity of apertures 8 through which sutures may pass to anchor the device to the patient's muscle fascia. The housing 2 includes an interior open-faced reservoir 9 defined by lateral surface 5 and bottom surface 6. As shown, reservoir 9 is cylindrical (having diameter D), extending along central axis A, with a circular cross-section perpendicular to central axis A. In other embodiments, reservoir 9 may be "substantially cylindrical", including functionally equivalent geometries, such as having an elliptical or polygonal cross-section perpendicular to central axis A.

The open face of reservoir 9 is spanned by a self resealing penetrable septum 3 which is held in place by a retaining element 4 which is press-fit into the housing 2. The housing 2 includes an outlet P from which an outlet cannula 11 extends. In the illustrated embodiment, cannula 11 extends from the housing 2 at a first end 11A (where it is integral with housing 2 at outlet P) to a second end 11B which is adapted to receive a catheter 13.

Figure 3:
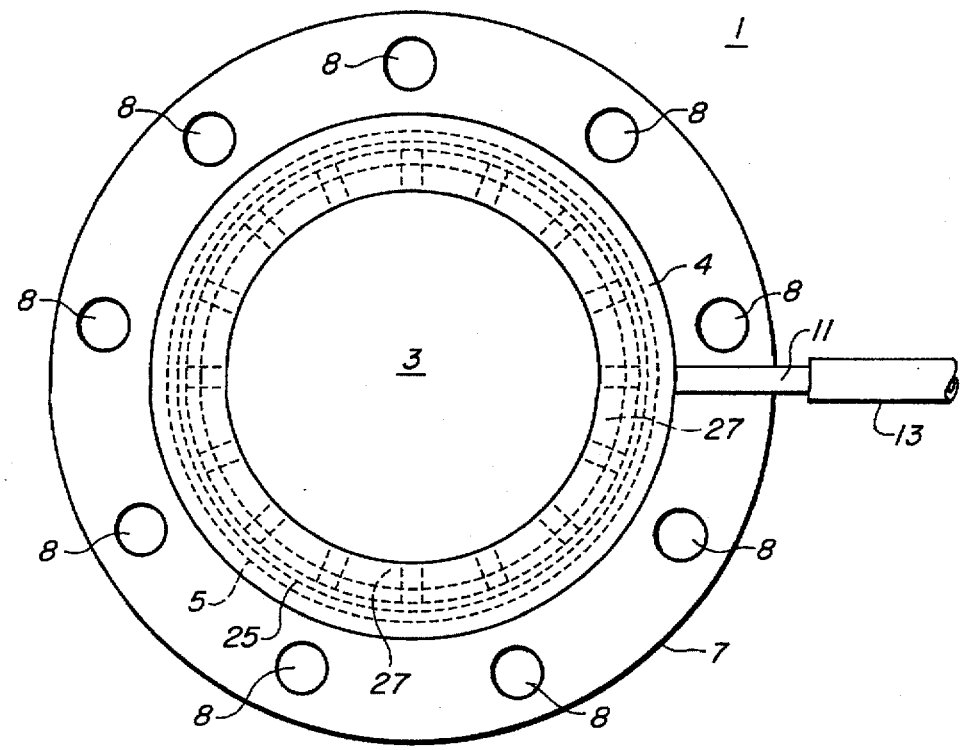
FIG. 3 shows a top plan view of the device of FIGS. 1 and 2.

A two-stage filter assembly 20 is shown installed within reservoir 9, under septum 3. Also shown in FIG. 1 is the lateral surface 5 of the reservoir 9. As shown in FIGS. 1 through 3, filter assembly 20 comprises a fluid permeable first wall 25 (stage 1) and a fluid permeable second wall 27 (stage 2). First wall 25 is substantially cylindrical and has a diameter $D_W$, which is less than D. That wall 25 is fluid permeable and is located interior to and spaced apart from the lateral surface 5 of reservoir 9 to allow a full 360° of fluid flow through the first annular chamber 32 established between first wall 25 and lateral surface 5. First wall 25 also establishes a first reservoir chamber 30 interior to first wall 25 and underlying septum 3. In the embodiment of FIGS. 1 through 3, chamber 30 houses second wall 27 which divides that chamber 30 to form second annular chamber 34 on one side of wall 27, with the remainder of chamber 30 on the other side of, and interior to, wall 27, as described in detail below.

The first annular chamber 32 and the first reservoir chamber 30 (as a whole) are in fluid communication only through first wall 25. In accordance with the invention, first wall 25, as shown in FIGS. 2 and 3, functions to remove particulate material from fluid injected into first reservoir chamber 30 prior to entry of that fluid into chamber 32 and eventually into internal channel 12 within and defined by outlet cannula 11. Internal channel 12 extends from the first end 11A of outlet cannula 11 along a channel axis CA from points on the lateral surface 5 of reservoir 9, to the second end 11B of outlet cannula 11. In accordance with the invention, channel 12 is in direct fluid communication only with first annular chamber 32.

The structure of first wall 25 may be selected to produce desired filtering capability. For example, first wall 25 may be formed from a mesh screen, the porosity of which may also be varied to achieve desired filtering and fluid flow rates. In the various forms of the invention different mesh sizes may be used, or alternatively, different forms of filter material may be used.

As shown in FIGS. 2 and 3, second wall 27 is also "substantially cylindrical" and fluid permeable, being placed interior to and spaced apart from first wall 25, establishing a second annular chamber 34 within first reservoir chamber 30 and between first wall 25 and second wall 27. Second annular chamber 34 provides the only fluid flow paths between the first central portion (i.e., along central axis A) of reservoir chamber 30 and first annular chamber 32. Second wall 27 allows 360° of fluid flow through that wall 27 to chamber 32. In accordance with the present invention, second wall 27 may take the form of a toroidal substrate extending about central axis A, and having a plurality of radially extending apertures 35 extending therethrough (and providing the fluid flow paths). The apertures 35 provide filtering, removing particulate material that is too large to pass therethrough. The number and size of apertures 35 is selected to provide desired filtering and flow rates. In the embodiment of FIGS. 1 through 3, the substrate also supports first wall 25, which is affixed to that substrate.

In the embodiment of FIGS. 1 through 3, second wall 27 is shaped to create an upper cylindrical reservoir sub-chamber 36a and a lower cylindrical reservoir sub-chamber 36b, respectively, within first reservoir chamber 30 and underlying septum 3. The right-circular cylindrical geometry of those reservoir sub-chambers provides sharp right angle corners within first reservoir chamber 30. During the injection of fluid into the device through septum 3, accumulation of particulate material or other debris in those corners is promoted and, in some cases, particulate material and other debris is held in those corners by eddy currents.

Figure 4:
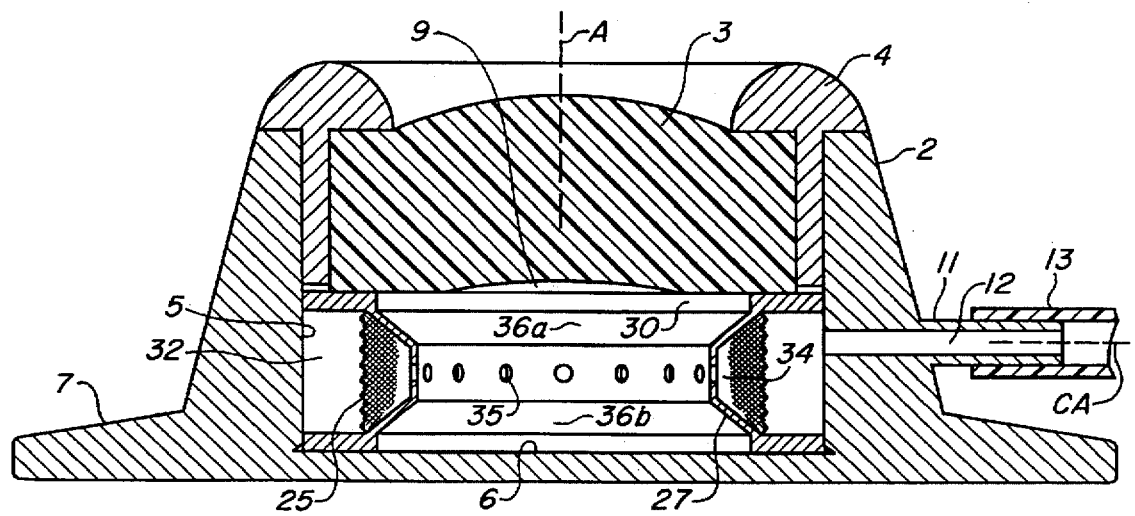
FIGS. 4, 5 and 6 show sectional views of additional embodiments of two-stage filter access devices of the invention.
Figure 5:
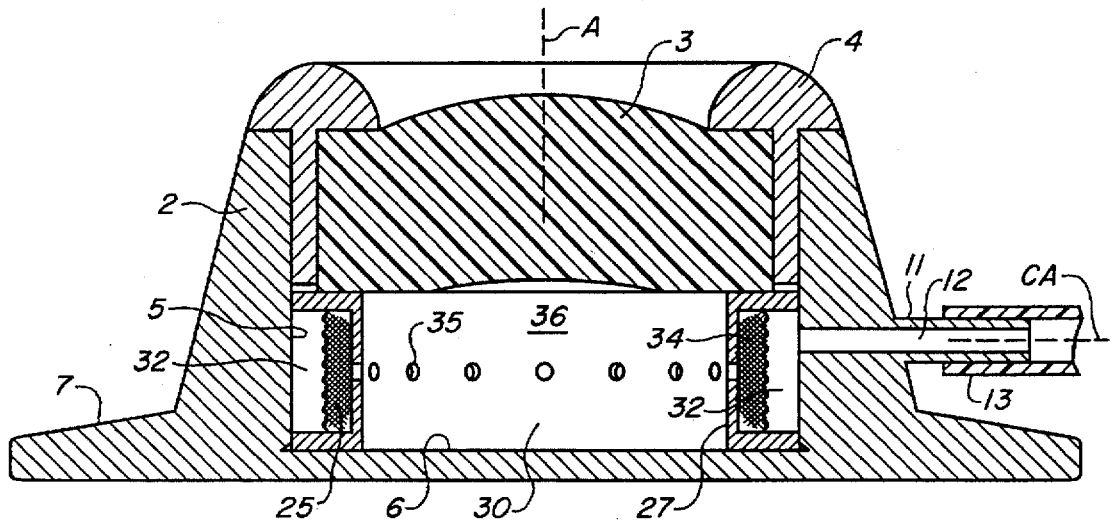
Figure 6:
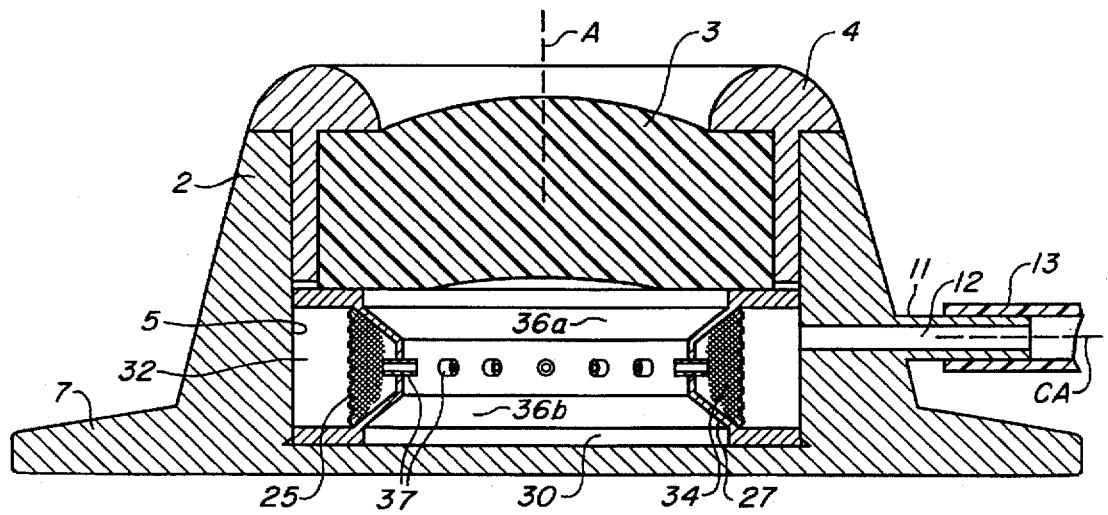

FIGS. 4 through 6 show three alternative embodiments, each of which is similar to the embodiment of FIGS. 1 through 3, but where the wall 27 differs, although it provides the same overall general function of the corresponding wall of the embodiment in FIGS. 1 through 3.

In the embodiment of FIG. 4, second wall 27 is shaped to create an upper inverted frustoconical reservoir sub-chamber 36a and a lower frustoconical reservoir sub-chamber 36b, respectively, within first reservoir chamber 30 and underlying septum 3. The reservoir sub-chambers 36a and 36b create relatively sharp or "acute" corners within first reservoir chamber 30, which promote the accumulation of particulate material, or other debris, when fluid is injected into the device. Those corners may have piecewise linear cross-sections, as illustrated in the embodiments of FIGS. 4 and 6; alternatively, those corners may have an eccentric concave curved cross-section, for example. All of such acute corners may function to accumulate particulate materials or other debris.

In the embodiment of FIG. 5, the wall 27 has a cylindrical form, with the apertures 35 passing therethrough. In that embodiment, the upper and lower sub-chambers 36a and 36b are effectively merged (and are denoted collectively in FIG. 5 by reference designation 36).

The embodiment of FIG. 6 is substantially similar to that of FIG. 4, with the apertures 35 each including a tube 37 extending therethrough and projecting into second annular chamber 34. The tubes 37 also project into first reservoir chamber 30, creating a plurality of "spikes" inside the chamber, creating additional recesses, cutouts, and sharp corners for entrapment of particulate material prior to entry into second annular chamber 34. Tubes may similarly be inserted into the apertures 35 of the embodiments of FIGS. 1 through 3 and FIG. 5 to create additional embodiments of the present invention.

Figure 7:
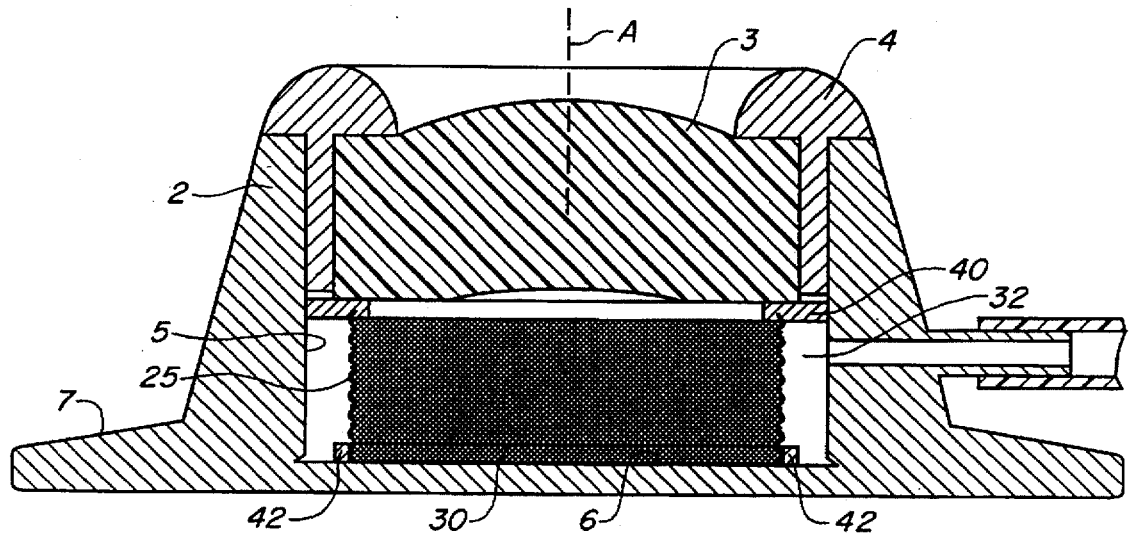
FIGS. 7 and 8 show sectional views of one-stage filter access devices of the invention.
Figure 8:
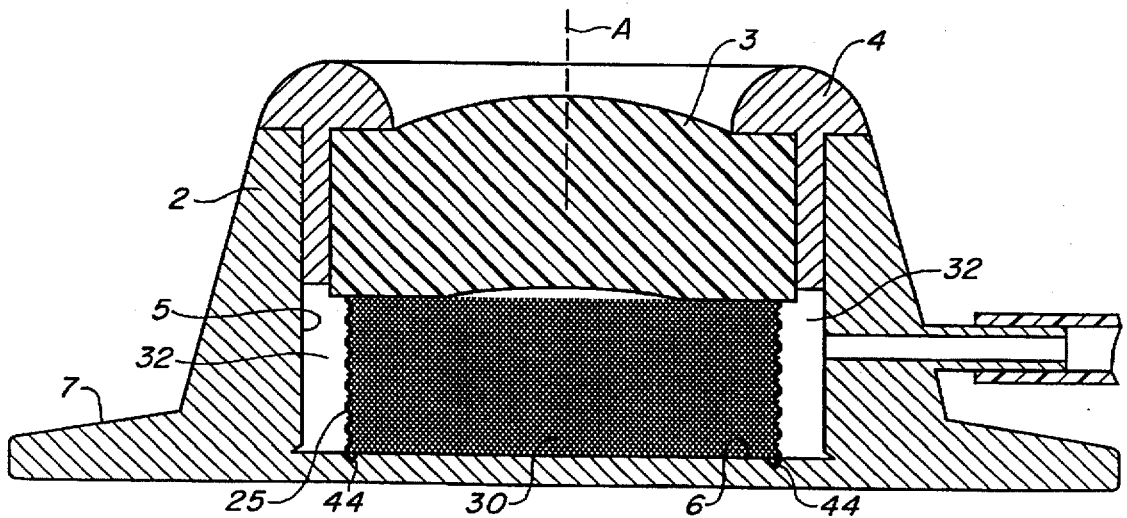

The embodiments of FIGS. 7 and 8 include only a single stage filter assembly, in contrast to the two-stage filter assembly shown in the embodiments of FIGS. 1 through 6. Filter assembly 20 of FIGS. 7 and 8 comprises first wall 25, affixed within reservoir 9 by a means for holding first wall 25 in place. First wall 25 establishes first annular chamber 32 between that wall and surface 5, and first reservoir chamber 30 interior to first wall 25 and underlying septum 30. As shown in FIGS. 7 and 8, first wall 25 is a mesh screen. In the embodiment of FIG. 7, first wall 25 extends from a rigid ring 40 and is held in place laterally within reservoir 9 by a ring support 42 extending from the bottom surface 6 of reservoir 9. The first wall 25 and ring 40 are held in place vertically by pressure from the retaining element 4 transferred through the septum 3. In the embodiment of FIG. 8, first wall 25 is held vertically by pressure from the retaining element 4 and transferred through septum 3, and laterally, that is, in a direction transverse to central axis A, by a circular positioning groove 44 in the base surface 6 into which wall 25 is positioned.

A filter assembly comprising filter assembly 20, suitable for insertion into an implantable access device, is another embodiment of the invention. The filter assembly embodiment of the invention may take any of the filter assembly configurations described in FIGS. 1 through 8, and includes means for positioning that filter within a cylindrical reservoir with the outer wall of the filter being spaced apart from the lateral wall of the reservoir, thereby allowing 360° of fluid flow through the filter. The size of implantable access devices is generally similar and uniform, as is well known in the art. As shown in FIG. 2, the reservoir 9 has a diameter D, and in accordance with the invention the filter assembly embodiment comprises a substantially cylindrical fluid permeable first wall defining a first reservoir chamber interior thereto and having at least a portion with maximum transverse diameter less than D and means for positioning the first wall within the reservoir 9 whereby an annular chamber is established between said portion and the lateral surface of the reservoir, said chamber being contiguous with the outlet port of the reservoir. The filter assembly embodiment of the invention may be used by inserting it into internal reservoir 9 of the housing 2 of an implantable access device prior to placement of septum 3.

Figure 9:
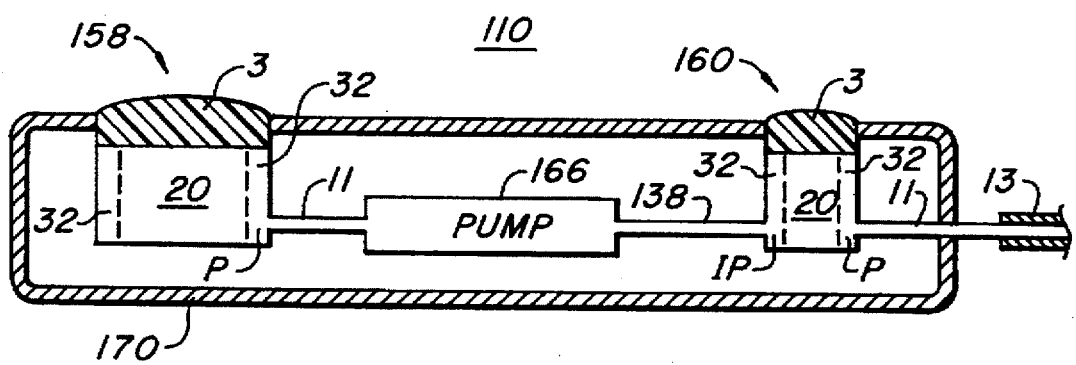
FIG. 9 shows a schematic representation, partly in section, of an infusion apparatus which incorporates two filter assemblies in accordance with the invention.

In other forms of the invention, one or more access devices with internal filter assemblies of the type described above, may also be functional components of an infusate pump apparatus, such as that disclosed in U.S. Pat. No. 4,496,343, incorporated herein by reference. FIG. 9 shows such an infusate pump apparatus 110, including two access ports (a primary access port 158 and a secondary, or side, access port 160), and including a pump 166, all within a biocompatible housing 170. The primary access port 158 is coupled to the input of pump 166 via cannula 11, and the output of pump 166 is coupled to the inlet port IP of side access port 160 via line 138. The pump 166 is selectively operative to drive fluid at its input to exit its output. For example, any of the septum-chamber filter configurations described in FIGS. 1 through 8 may be used for access ports 158 and 160, except that access port 160 has an input port IP (in addition to its output port P) attached to the outlet tube 138 extending from pump 166.

Although the side access port 160 is illustrated in FIG. 9 as being contained within a common housing 170, the present invention also encompasses embodiments in which the infusate pump apparatus and the side access port 160 are connected but not contained within a common housing.

Figure 10:
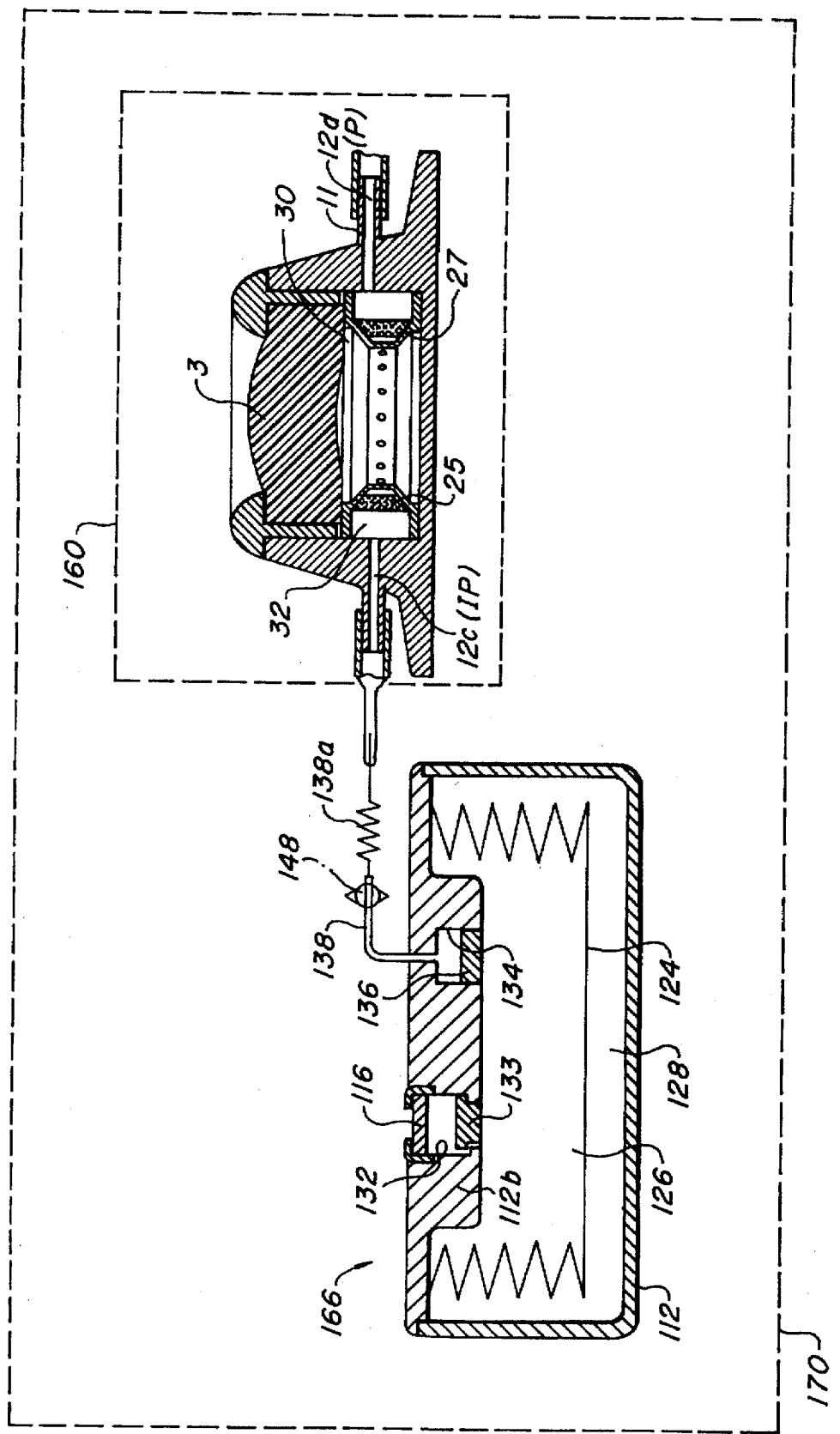
FIG. 10 shows in section an infusion apparatus which incorporates a filter assembly in accordance with the invention in a side-port configuration.

FIG. 10 shows a configuration for pump apparatus 110 that includes a pump 166 of the form shown in U.S. Pat. No. 4,496,343, together with a side access port of the form shown in FIG. 4 (augmented by port IP). In FIGS. 9 and 10, elements corresponding to similar elements in FIGS. 1 through 8 are denoted with the same reference designations.

As described in detail in U.S. Pat. No. 4,496,343, the implantable infusate apparatus or pump 166 comprises a generally cylindrical housing 112, which is about the size of a small hockey puck, and which is made of a suitable material that is compatible with the human system, such as titanium. Positioned in the housing 112 is a bellows capsule 124 having an open end mounted to a header 112b at the top of housing 112, the opposite end of the bellows capsule being closed. The bellows defines a first chamber 126 inside the bellows and a second chamber 128 outside the bellows, but inside housing 112. Formed in header 112b is an entry port 132 which extends from chamber 126 through header 112b. The outer end of entry port 132 is closed by self resealing penetrable septum 116. A porous needle stop 133 is positioned at the inner end of port 132. Also formed in the header is an exit port 134 containing a filter 136. That port communicates with outlet tube 138 containing fluid restrictor 138a, the opposite end of which communicates with input channel 12c of the side access port 160 of the invention.

In use, chamber 126 is filled with an infusate by injecting the infusate through septum 116. Chamber 128 is filled with a two-phase fluid that vaporizes at physiological temperatures, thus exerting pressure on bellows capsule 124 and tending to collapse it, thereby expelling the infusate through exit port 134 and restrictive outlet tube 138, into the first annular chamber 32 and first reservoir chamber 30 of the filter assembly of the present invention. A bolus of the same infusate, or of a different liquid may be injected through septum 3 into first reservoir chamber 30 of side access port 160. Since the restrictor 138a in line 138 provides a relatively high impedance path to the fluid in chamber 30, relative to the path in conduit 12d, the bolus injection flows through first annular chamber 32 into conduit 12d within outlet cannula 11 to the treatment site within the patent. As set forth above, any particulate material in the bolus liquid will be filtered out by the fluid dynamics created by the shape of the walls of first reservoir chamber 30. A second wall 27 may be present in the filter assembly, as shown in FIG. 10. Alternatively, the single stage filter assemblies of FIGS. 7 and 8 may be attached to the infusate apparatus pump 166 via outlet tube 138. In other forms of the invention, similar access ports may be used to provide primary infusate to the pump 166.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. An implantable access device comprising:
   A. a biocompatible housing defining an internal open-faced, substantially cylindrical reservoir defined by a lateral surface extending about a central axis and a bottom surface;
   B. a biocompatible, self-resealing, penetrable septum affixed to said housing and spanning the open face of said reservoir;
   C. an outlet extending through said housing along an outlet channel axis from a point on said lateral surface of said reservoir, and
   D. a filter assembly disposed in said reservoir, said filter assembly including a substantially cylindrical fluid permeable first wall interior to and spaced apart from said lateral surface of said reservoir, said first wall establishing a first annular chamber between said first wall and said lateral surface and a first reservoir chamber interior to said first wall and underlying said septum, said first annular chamber and said first reservoir chamber being in fluid communication only through said first wall, and said outlet being in direct fluid communication with said first annular chamber.

2. The implantable access device according to claim 1 further comprising an outlet cannula having a first end extending from said outlet and a second end adapted to receive a catheter, said outlet cannula further defining an internal channel extending from said first end, along said channel axis to said second end.

3. The implantable access device according to claim 1, wherein said filter assembly further includes:
   a substantially cylindrical fluid permeable second wall interior to and spaced apart from said first wall, said second wall establishing within said first reservoir chamber:
   i. a second annular chamber between said second wall and said first wall; and
   ii. at least one reservoir sub-chamber interior to said second wall and underlying said septum;
   said second annular chamber being in fluid communication with said reservoir sub-chamber only through said second wall and being in fluid communication with said first annular chamber only through said first wall.

4. The implantable access device according to claim 3 wherein said filter assembly includes a substrate extending about said central axis, said substrate forming said second wall and supporting said first wall.

5. The implantable access device according to claim 4, wherein said substrate is a rigid material having a plurality of passages extending therethrough.

6. The implantable access device according to claim 5, wherein each of said passages contains a tube extending therethrough.

7. The implantable access device according to claim 5, wherein said first wall is a mesh screen.

8. The implantable access device according to claim 4, wherein said filter assembly further comprises a second reservoir sub-chamber interior to said second wall and adjacent to the bottom surface of the reservoir.

9. The implantable access device according to claim 8, wherein said substrate is a rigid material having a plurality of passages extending radially therethrough.

10. The implantable access device according to claim 9, wherein each of said passages contains a tube extending therethrough.

11. The implantable access device according to claim 8, wherein said reservoir sub-chambers comprise one or more acute corners in their defining surfaces.

12. The implantable access device according to claim 4, wherein said first wall is a mesh screen.

13. The implantable access device according to claim 3, wherein said reservoir sub-chamber is defined by surfaces that establish a principal fluid flow path extending in said reservoir sub-chamber and through said second wall, and establish one or more eddy flow paths that are substantially within said reservoir sub-chamber.

14. The implantable access device according to claim 3, wherein said reservoir sub-chamber are substantially cylindrical.

15. The implantable access device according to claim 3, wherein said reservoir sub-chamber are substantially frustoconical.

16. The implantable access device according to claim 3, wherein said first wall is a mesh screen.

17. The implantable access device according to claim 1, wherein said first wall is a mesh screen.

18. The implantable access device according to claim 17, wherein the bottom surface of the reservoir further includes a positioning groove adapted to interfit with said filter screen, whereby the position of the mesh screen is substantially fixed in a direction transverse to said central axis.

19. The implantable access device of claim 1, further comprising an infusion pump apparatus, said infusion pump apparatus including an input, an output and a pump for selectively driving fluid entering said input to exit said output, and coupling means for coupling at least one of said input and said output of said pump apparatus to said implantable access device.

20. The implantable access device of claim 19, wherein said coupling means includes means for coupling said outlet port of said implantable access device to said input of said infusion pump apparatus.

21. The implantable access device of claim 20, wherein said implantable access device and said infusion pump apparatus are contained within a common housing.

22. The implantable access device of claim 19, wherein said implantable access device further includes an inlet extending through said housing along an inlet channel axis to a point on said lateral surface of said reservoir, and wherein said coupling means includes means for coupling said output of said infusion pump apparatus to said inlet of said implantable access device.

23. The implantable access device of claim 22, wherein said implantable access device and said infusion pump apparatus are contained within a common housing.

24. A filter assembly for placement within a cylindrical reservoir of an implantable access device, said reservoir being defined by a cylindrical lateral surface having diameter D and extending along a reference axis, and at one end by a bottom surface transverse to said reference axis and at an end opposite said bottom surface by a self-sealing, penetrable septum spanning said reservoir, and having an outlet extending from said lateral surface, comprising:
  i. a substantially cylindrical fluid permeable first wall defining a first reservoir chamber interior thereto and having at least a portion with maximum transverse diameter less than D and
  ii. means for positioning said first wall within said reservoir whereby an annular chamber is established between said portion and said lateral surface of said reservoir, said chamber being contiguous within said outlet port,
wherein the first wall is a mesh screen.

25. The filter assembly according to claim 24, further including a substantially cylindrical fluid permeable second wall interior to and spaced apart from said first wall, said second wall establishing within said first reservoir chamber a second annular chamber between said second wall and said first wall.

26. The filter assembly according to claim 25, wherein the second wall comprises a substantially rigid toroidal substrate extending about an axis and having a plurality of passages extending radially therethrough.

27. The filter assembly according to claim 26, wherein each of said passages contains a tube extending therethrough.

28. A filter assembly for placement within a cylindrical reservoir of an implantable access device, said reservoir being defined by a cylindrical lateral surface having diameter D and extending along a reference axis, and at one end by a bottom surface transverse to said reference axis and at an end opposite said bottom surface by a self-sealing, penetrable septum spanning said reservoir, and having an outlet extending from said lateral surface, comprising:
  i. a substantially cylindrical fluid permeable first; wall defining a first reservoir chamber interior thereto and having at least a portion with maximum transverse diameter less than D and
  ii. means for positioning said first wall within said reservoir whereby an annular chamber is established between said portion and said lateral surface of said reservoir, said chamber being contiguous within said outlet port, and
further including a substantially cylindrical fluid permeable second wall interior to and spaced apart from said first wall, said second wall establishing within said first reservoir chamber:
  i. a second annular chamber between said second wall and said first wall; and
  ii. a first reservoir sub-chamber interior to said second wall; said sub-chamber being interior to said second wall and said second annular chamber being in fluid communication with said reservoir sub-chamber only through said second wall.

29. The filter assembly according to claim 28, wherein the second wall comprises a substantially rigid toroidal substrate extending about an axis and having a plurality of passages extending radially therethrough.

30. The filter assembly according to claim 28, further comprising a second reservoir sub-chamber interior to the second wall.

31. The filter assembly according to claim 30, wherein the first and second reservoir sub-chambers are substantially cylindrical.

32. The filter assembly according to claim 30, wherein the first and second reservoir sub-chambers are substantially frustoconical.

* * * * *